United States Patent
Raupach

(10) Patent No.: US 6,600,801 B2
(45) Date of Patent: Jul. 29, 2003

(54) METHOD FOR CORRECTING FOR BEAM HARDENING IN A CT IMAGE

(75) Inventor: Rainer Raupach, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 33 days.

(21) Appl. No.: 09/981,478

(22) Filed: Oct. 17, 2001

(65) Prior Publication Data
US 2002/0097830 A1 Jul. 25, 2002

(30) Foreign Application Priority Data
Oct. 17, 2000 (DE) .......................................... 100 51 462

(51) Int. Cl.[7] .................................................. A61B 6/03
(52) U.S. Cl. .......................................... 378/4; 378/901
(58) Field of Search ................................ 378/4, 5, 6, 7, 378/16, 901

(56) References Cited

U.S. PATENT DOCUMENTS

| | | | |
|---|---|---|---|
| 4,217,641 A | 8/1980 | Naparstek | 364/414 |
| 5,848,114 A * | 12/1998 | Kawai et al. | 378/4 |
| 6,035,012 A | 3/2000 | Hsieh | 378/4 |
| 6,094,467 A * | 7/2000 | Gayer et al. | 378/4 |
| 6,101,236 A * | 8/2000 | Wang et al. | 378/4 |
| 6,421,411 B1 * | 7/2002 | Hsieh | 378/4 |

OTHER PUBLICATIONS

"Optimierung an der Quelle," Dieberger, C't, vol. 3 (1991) pp. 302–312.

* cited by examiner

*Primary Examiner*—Louis Arana
(74) *Attorney, Agent, or Firm*—Schiff Hardin & Waite

(57) ABSTRACT

A method for correcting for beam hardening in an initial CT image, which is composed of pixels arranged in a matrix, correction data are determined from the initial image by re-projection of the pixels from the initial image at a large number of projection angles, the pixels from the initial image being compared with a threshold value for each of the projection angles during the re-projection, and the re-projection being carried out for only those pixels from the initial image which have a pixel value above the threshold value. The correction data are used to determine a corrected image from the initial image.

5 Claims, 2 Drawing Sheets

METHOD FOR CORRECTING FOR BEAM HARDENING IN A CT IMAGE

BACKGROUND OF THE INVENTION

1. Field of the Invention

The present invention relates to a method correcting for beam hardening in a CT (computed tomography) image, which is composed of pixels arranged in a matrix, of the type wherein correction data are obtained from an initial CT image by re-projecting the pixel from the initial image at a large number of projection angles, with pixels from the initial image being compared with a threshold value for each of the projection angles during the re-projection, and the correction data are used to determine a corrected image from the initial image.

2. Description of the Prior Art

A method of this above type is disclosed, for example, in U.S. Pat. Nos. 6,035,012 and 4,217,641.

Because of the spectral dependence of the beam attenuation behavior of real bodies in the case of polychromatic X-rays a shift in the average energy of the X-rays emerging from an irradiated body toward higher energy values occurs. This effect is referred to as beam hardening. In the reconstructed image of the body, this effect is manifested as deviations in the gray-scale value as compared with the theoretical case of linear, spectrally independent beam attenuation. The gray-scale value deviations—or beam hardening artefacts—caused in particular by materials with a high atomic number and density (for example bones) in the reconstructed image interfere with the diagnostic content of the image and, in the worst case, can lead the investigating physician to misinterpretation. The beam hardening correction is carried out in order to eliminate these artefacts, at least to some extent.

In known methods of the type initially mentioned, the procedure operates such that, for the individual projection angle and before the re-projection, those pixels which lie below the threshold value are set to zero before the re-projection of the entire pixel matrix is carried out.

For the re-projection, substantially two methods are considered:

Inverse Fourier Reconstruction Methods

The complete integral transformation of the image reconstruction of the initial image is made reversible (see U.S. Pat. No. 4,616,318). In particular, effects which are caused by the reconstruction core, such as cupping correction and so on, can be corrected in this way. The complexity of inverse Fourier reconstruction methods is very high, so that an application in real time is not readily possible in practice.

Ray-tracing Algorithms

Starting from the pixel matrix of the initial image, the corresponding parallel projections are determined directly by approximate calculation of the linear integral. Ray-tracing algorithms fall into two classes: (a) pixel-intercepting methods and (b) forward-projection methods (FPM). Both methods are pixel-driven in the sense that no projection beams are specified, but instead the pixel co-ordinates are the starting point for the assessment of contributions to the attenuation. In this way, the influence of the reconstruction kernel cannot be taken into account. In the case of kernels without a cupping correction being used, however, this proves to be unnecessary for the first image reconstruction.

In the following, the procedure in the FPM described in T. M. Peters, "Algorithms for fast back- and re-projection in computed tomography" IEEE Trans. Nucl. Sci., vol. NS-28, pp. 3641–3647, 1981, is outlined as an example of a pixel-oriented algorithm.

Let the starting point be an initial image having N×N square pixels. If b is the edge length of a pixel, then the result for the coordinates of the center of the pixel (n,n') in a rectangular coordinate system having the axes x and y is $$x_n = nb, \; y_{n'} = n'b.$$

A predefined set of parallel beams is defined by the angle $\theta$ with respect to a fixedly chosen reference axis, for example the y axis. The distance of the pixel (n,n') from the origin (=pixel (0,0)) is therefore given by $$t = x_n \cos \theta + y_{n'} \cos \theta.$$

If a is the distance of the parallel beams from one another, then the selected pixel (n,n') is consequently located between the beams K and K+1, it being true that $$K \leq t/a < K+1.$$

In order to decide the manner in which the pixel value $P_{n,n'}$ contributes to the attenuation integral, the weighting factor $$a_K = t/a - K (0 \leq a_K < 1)$$

is calculated, and the contribution to the adjacent beams is given as $$S(K) \rightarrow S(K) + (1 - a_K) P_{n,n'},$$

$$S(K+1) \rightarrow S(K+1) + a_K P_{n,n'}.$$

It is obvious that the number of beams plays no part in the complexity of the algorithm. If $N_p$ is the number of projections of the parallel data, then the run time of a complete image reconstruction is on the order of $N_p \cdot N^2$.

For a practical application of FPM in the course of a beam hardening correction, the run time primarily plays a significant part. A first starting point for optimizing the run time is to reduce the size of the image matrix, which corresponds to a reduction in the maximum frequency contained in the image. This leads to "fading" of the contrast, which is tolerable only within certain limits, since the accuracy of the determined bone thickness in the correction method does not necessary have to be on the order of magnitude of the pixel size in order to achieve usable results. In the event of linear shrinkage of the image size by the factor c, the computing outlay is reduced by the factor $c^2$, because of the orientation of the pixels.

General measures which can lead to a reduction in the computing time are described in the article by Dieberger, A.: Optimierung an der Quelle [optimization at the source], part 3, c't, volume 3, 1991, pp. 302–312.

SUMMARY OF THE INVENTION

An object of the present invention is to provide a method of the type initially described wherein a reduction in the run time is also possible without any reduction in the size of the image matrix.

According to the invention, this object is achieved by a method of correcting for beam hardening for an initial CT image, which is composed of pixels arranged in a matrix, having the following method steps, correction data are determined from the initial image by re-projecting the pixels from the initial image at a large number of projection angles, the pixels from the initial image being compared with a threshold value for each of the projection angles during the re-projection, and the re-projection being carried out only for those pixels from the initial image whose pixel value lies above the threshold value, and the correction data are used to determine a corrected image from the initial image.

The invention makes use of the fact that, to decrease the attenuation contribution resulting from hardening materials, only the pixels from the image which lie above the threshold value, those pixels whose pixel value (CT number) lies above a threshold value that is critical for the respective material, are relevant. In the case of bones, for the case in which a beam hardening correction is desired, for example in the area of the base of the skull, experience shows that these are less than 20% of the pixel from the initial image.

It is therefore sufficient, according to the invention, when determining correction data to include only those pixels from the initial image in the re-projection, whose pixel value lies above the threshold value, i.e., to carry out the re-projection only for those pixels.

Because of the reduction in the number of pixels to be taken into account, this permits time optimization of the re-projection operation without reducing the quality of the data produced, in particular the parallel data.

In a first embodiment of the invention, for each of the projection angles during the re-projection, those pixels on the initial image are determined whose pixel value lies above the threshold value.

In this case, given linear indexing of the image matrix, the index of the loops to be executed for the respective projection runs from 1 to $N^2$. Since, for each pixel, it is directly determined whether its pixel value lies above the threshold value, the actually time-consuming steps such as the reconstruction of the two-dimensional co-ordinates of the pixel have to be carried out only for those pixels whose pixel value lies above the threshold value. If a is the proportion of the pixels that contributes to a projection, i.e., that lie above the threshold value, as compared with the number of all the pixels in the initial image, then an acceleration by the factor $\alpha^{-1}$ occurs with respect to the time-consuming steps. Because of the loop overhead, (the run time which is needed in order to determine the pixels whose pixel value lies below the threshold value), this theoretically possible acceleration is, however, not achieved overall.

In a further embodiment of the invention, before the re-projection of the initial image, those pixels from the initial image are determined and saved whose pixel value lies above the threshold value, and for each of the projection angles, these saved pixels lying above the threshold value are used for the purpose of re-projection. Thus, a speed-up does occur, which comes very close to the theoretically possible factor of $\alpha^{-1}$, since, in addition to the run time necessary for the reconstruction of the relevant pixels, (those lying above the threshold value), the run time which additionally arises is only that which is needed to determine the relevant pixels once. The actual loop for the re-projection for each projection angle runs through an index from 1 to $\alpha \cdot N$. In practice, the acceleration can be even greater than $\alpha^{-1}$, for example because of accesses to the cache memory of the electronic computing device carrying out the described operations.

In this case, in a preferred embodiment of the invention, the pixels from the initial image whose pixel value lies above the threshold value are saved in a data set which, for each pixel lying above the threshold value, contains the two-dimensional co-ordinates of the center of the pixel and the associated pixel value. As compared with the possible saving of the relevant pixels in a data set which contains the linear index and the pixel value, which is also possible according to an embodiment of the invention, this embodiment offers the run-time advantage that the two-dimensional co-ordinates of the relevant pixels needed for the re-projection have to be calculated only once.

DESCRIPTION OF THE PREFERRED EMBODIMENTS

Figure 1:
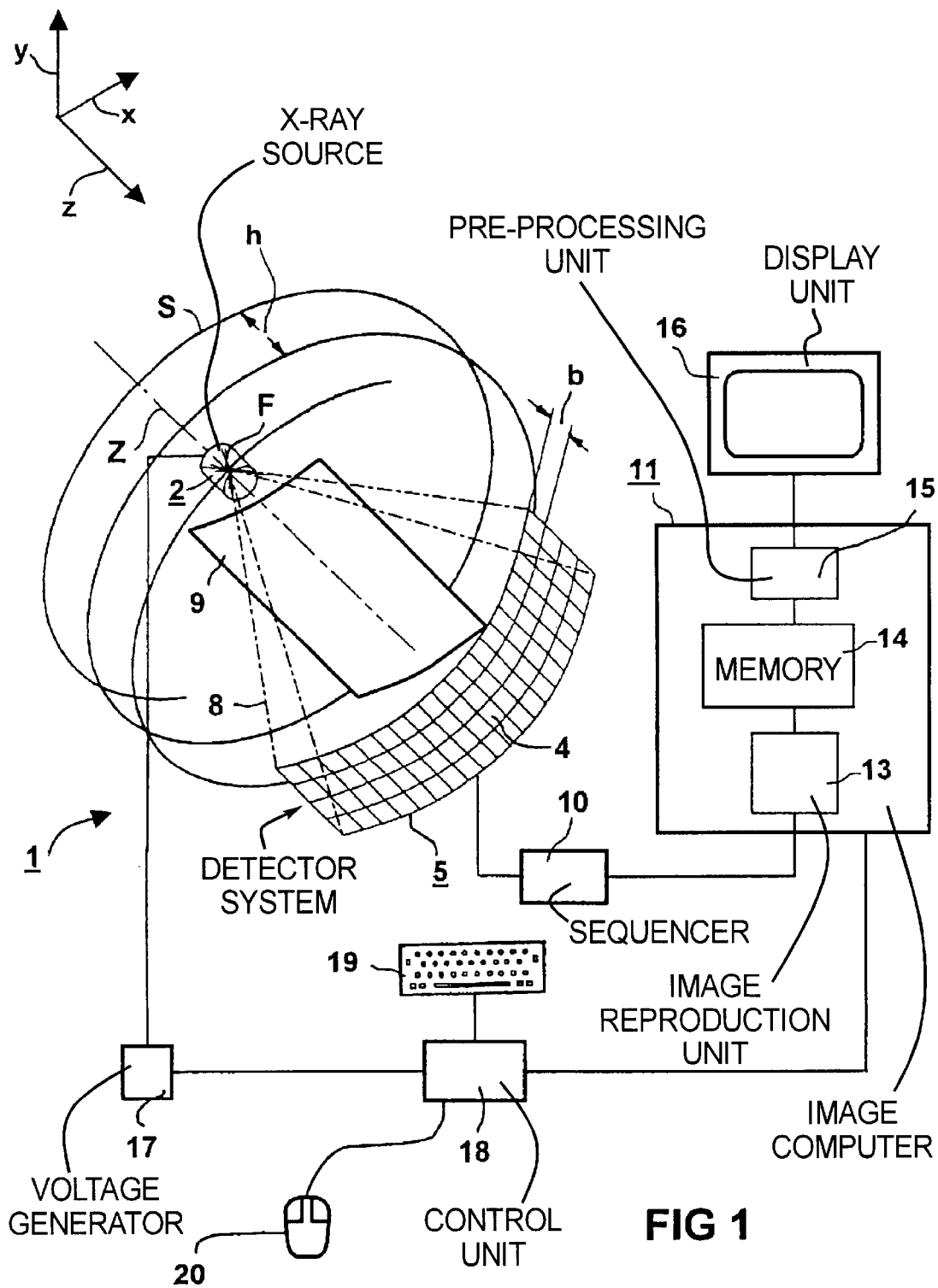
FIG. 1 shows, in a schematic block diagram, a CT apparatus suitable for carrying out the method according to the invention.
Figure 2:
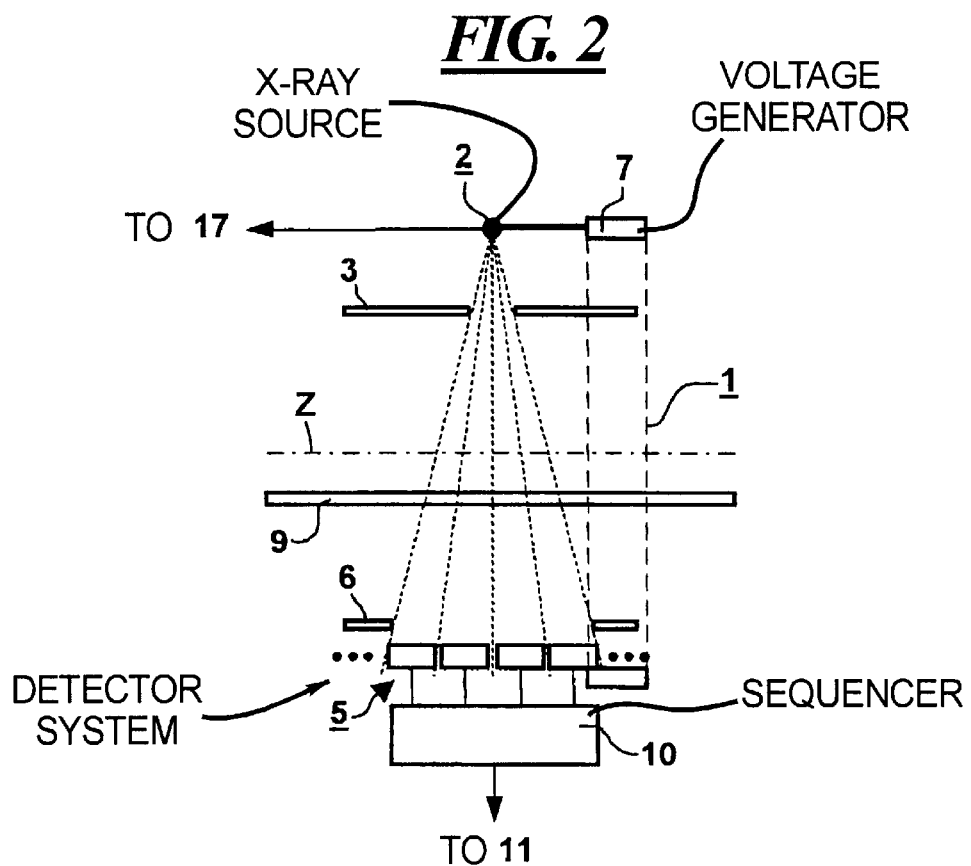
FIG. 2 shows a longitudinal section through the apparatus of FIG. 1.

FIGS. 1 and 2 show a multi-layer CT apparatus of the third generation suitable for carrying out the method according to the invention. Its measuring arrangement has an X-ray source 2 with a beam diaphragm 3 (FIG. 2) located in front of and close to the source 2. The arrangement 1 also has a detector system 5 constructed as a two-dimensional array of a number of rows and columns of detector elements—one designated by 4 in FIG. 1—with a beam diaphragm 6 located in front of and close to the detector system 5 (FIG. 2). The X-ray source 2 with the beam diaphragm 3 and the detector system 5 with the beam diaphragm 6 are mounted opposite each other on a rotating gantry 7, as shown in FIG. 2, so that a pyramid-like bundle of X-ray which originates from the X-ray source 2, is collimated by the adjustable beam diaphragm 3, with edge rays 8 is incident on the detector system 5. In this case, the beam diaphragm 6 is set to correspond to the cross section of the bundle of X-rays set by means of the beam aperture 3 so that only that area of the detector system 5 is exposed which can be struck directly by the bundle of X-rays. In the operating state illustrated in FIGS. 1 and 2, these are four rows of detector elements. The fact that further rows of detector elements covered by the beam diaphragm 6 are present is indicated by dots in FIG. 2.

The rotating frame 7 is rotated around a system axis Z by means of a drive device (not illustrated). The system axis Z is parallel to the z axis of a three-dimensional rectangular co-ordinate system illustrated in FIG. 1.

The columns of the detector system 5 likewise proceed in the direction of the z axis, while the lines, whose width b is measured in the direction of the z axis and is, for example, 1 mm, proceed transversely with respect to the system axis Z and to the z axis.

In order to be able to bring an object to be examined, for example a patient, into the beam path of the bundle of X-rays 2, a support device 9 is provided, for example in the form of a patient table, which can be displaced parallel to the system axis Z, i.e., in the direction of the z axis.

In order to record volume data from an object to be examined and located on the support device 9, the object to be examined 23 is scanned by a large number of projections recorded from various projection directions while the measuring unit 1 is moved around the system axis Z. Data are obtained from a measuring field 22 of circular cross section, in which the object to be examined is located.

During the continuous rotation of the measuring unit 1 around the system axis Z, at the same time the support device 9 is displaced continuously in the direction of the system axis Z and relative to the measuring unit 1, synchronized with the rotation of the rotating frame 7 and the translational movement of the mounting device 9 with the effect that the ratio of translational to rotational speed being constant, this constant ratio being adjustable. This is accomplished by selecting a value for the advance h of the mounting device 9 for each revolution of the rotating frame 7 which ensures complete scanning of the volume of interest of the object to be examined. The focus F of the X-ray source 2, as viewed from the object being examined, therefore moves on a helical spiral path, designated by S in FIG. 1, around the system axis Z, for which reason the above-described type of recording volume date is also referred to as spiral scanning or spiral scan. The volume data are supplied by the detector elements of each line of the detector system 5 as projections respectively associated with a specific line of the detector system 5 and a specific position with respect to the system axis Z. The volume data are read out in parallel, serially converted in a sequencer 10, and transmitted to an image computer 11.

Following preprocessing of the volume data in a preprocessing unit 15 of the image computer 11, the resulting data stream passes to a memory 14, in which the volume data corresponding to the data stream are saved.

The image computer 11 contains a reconstruction unit 13, which reconstructs image data from the volume data, for example in the form of sectional images of desired slices of the object to be examined 23, in accordance with methods known to those skilled in the art. The image data reconstructed by the reconstruction unit 13 are saved in the memory 14 and can be displayed on a display unit 16, for example a video monitor, connected to the image computer 11. In this case, the image computer 11 can effect beam hardening correction of reconstructed image data if required before the display.

The X-ray source 2, for example an X-ray tube, is supplied with the necessary voltages and currents by a generator unit 17. In order to be able to adjust these to the respective requisite values, the generator unit 17 is connected to a control unit 18 with a keyboard 19 and mouse 20, which permits the necessary adjustments.

In addition, the other operation and control of the CT apparatus is carried out by means of the control unit 18 and the keyboard 19 and also the mouse 20, which is illustrated by the fact that the control unit 18 is connected to the image computer 11.

A sectional image is saved in the memory 14 in the form of a data set which, for each pixel, contains the linear index and the pixel value (CT number) converted into a gray-scale value according to a gray-scale value table in the image display.

In the course of the beam hardening correction in accordance with the method of the invention, for each reconstructed sectional image saved in the memory 14 (referred to below as an initial image), those pixels are identified which have a pixel value lies above a threshold value. This threshold value is, for example, a CT number of 180 HU (Hounsfield Units) for bone. By re-projecting these pixels for a large number of projection angles, correction data are determined which are used to produce image data corrected for the effect of beam hardening.

Figure 3:
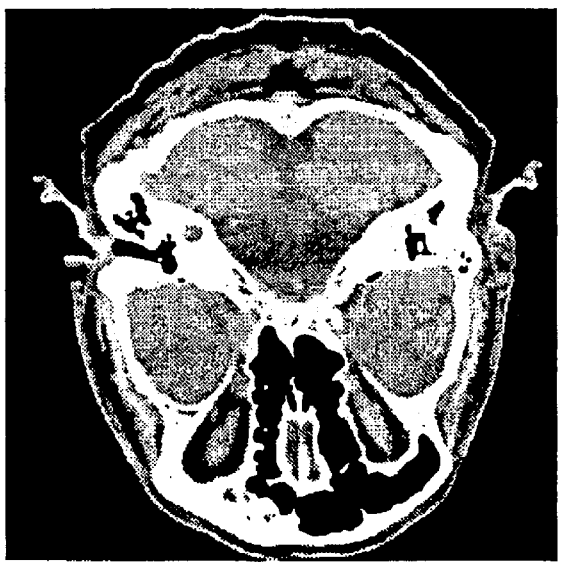
FIGS. 3 and 4 show sectional images for explaining the method according to the invention.

The initial image, composed of pixels arranged in a matrix, for example in accordance with FIG. 2, can be a typical sectional image of a human skull. For the case in which, in order to correct the beam hardening caused by bone, those pixels are taken to be relevant which have a pixel value above a CT number of 180 HU. Then only those pixels contained in the threshold-value image, as shown in FIG. 3, are taken into account in the re-projection needed for the beam hardening correction. In the example according to FIGS. 3 and 4, these are 12.7% of the pixels from the initial image. This corresponds to a value of $\alpha^{-1}$ of about 8.

In a first mode of operation of the CT apparatus, corresponding to a first embodiment of inventive the method, for each of the projection angles, during the re-projection, those pixels from the initial image are determined whose pixel value lies above the threshold value.

Only in connection with the decision as to whether a pixel lies above the threshold value, which is less expensive in terms of run time, is it necessary for the loop executed by the image computer 11 for each projection to register all the pixels. Since, however, it is decided directly for each pixel whether it lies above the threshold value, it is necessary to carry out the time-consuming steps, i.e., the reconstruction of the two-dimensional co-ordinates of the pixel, only for those pixels which lie above the threshold value. If, therefore $\alpha$ is the proportion of the pixels that contribute to a projection and therefore lie above the threshold value, in relation to the number of all the pixels from the initial image, then there is a speed-up by a factor $\alpha^{-1}$ with respect to the time-consuming steps.

This also becomes clear from Table 1 below, which shows that, in the first operating mode for the example according to FIGS. 3 and 4, a reduction in the run time by a factor of about four is achieved, the theoretically achievable factor being about eight.

In a second operating mode of the CT apparatus, corresponding to a second embodiment of the method according to the invention, those pixels from the initial image whose pixel value lies above the threshold value are determined and saved (stored) before the re-projection. For the purpose of re-projection, for each of the projection angles, recourse is then made to the saved pixels lying above the threshold value. The pixels from the initial image whose pixel value lies above the threshold value are saved in a data set which, for each pixel lying above the threshold value, contains the two-dimensional co-ordinates of the center of the pixel and the associated pixel value, the co-ordinates of the centers of the pixels being calculated by the image computer 11 before being saved.

Since, in the second operating mode, the pixels from the initial image whose pixel value lies above the threshold value are determined and saved in advance for all projection angles, it is possible, for the individual projection angles, to have recourse to the saved pixels lying above the threshold value for the purpose of re-projection. A speed-up therefore occurs, which comes very close to the theoretically possible factor of $\alpha^{-1}$ since, in addition to the run time needed for the reconstruction of the pixels lying above the threshold value, only that run time additionally arises which is needed for the single determination of the pixels lying above the threshold value. If the image computer 11 has a cache memory, the speed-up can be even greater than $\alpha^{-1}$, for example because of time-saving accesses to the cache memory.

Figure 4:
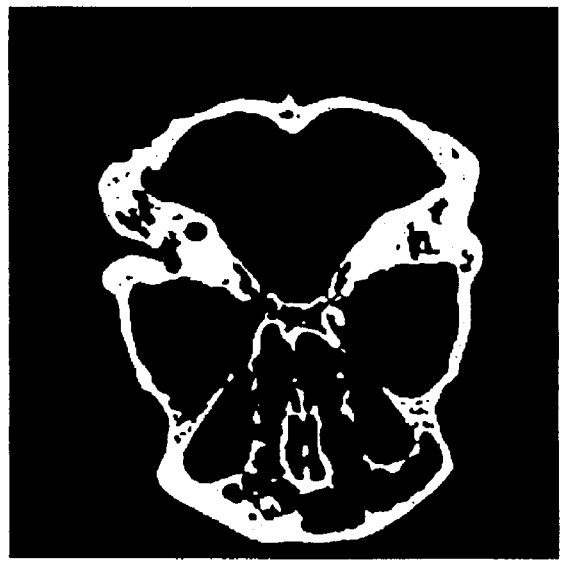

As Table 1 shows, in the second operating mode for the example according to FIGS. 3 and 4, a reduction in the run time of a factor of about eight is achieved, which corresponds to the theoretically achievable factor of about eight.

Following the determination of the correction data, on the basis of the correction data, a correction is made to the original data on the basis of the correction data in a manner known per se, for example with the aid of look-up tables.

On a standard PC with a Pentium III® (650 MHZ) processor, in the example according to FIGS. 3 and 4, for the FPM discussed as prior art and the two operating modes described above, for different sizes of the image matrix from the initial image and a number of $N_p=580$ projections, the following values are achieved for the run time:

TABLE 1

| Size of the image matrix | Run time[s] Standard FPM | Run time[s] First operating mode | Run time[s] Second operating mode |
|---|---|---|---|
| 512 × 512 | 35.2 | 9.2 | 4.0 |
| 256 × 256 | 8.8 | 2.3 | 1.0 |
| 128 × 128 | 2.1 | 0.56 | 0.25 |

It can also be seen from Table 1 that, in the second operating mode, in which run times are achieved which are less than 12% of the run time achieved in accordance with the prior art, the theoretically possible value of 12.7% for the present example can actually be undershot in practice.

In the second operating mode, during the saving of the pixels whose pixel value lies above the threshold value, the memory of the CT appliance can be operated in an alternative storage mode which, for each of these pixels, contains the linear index and the pixel value. This storage mode on the basis of linear indexing of the pixels corresponds to the procedure which is usual in CT appliances, but has the disadvantage of a slightly higher run time.

In the above exemplary embodiment, the beam hardening correction is described as a single procedure. In practice, however, it may be necessary to carry out the beam hardening correction in an iterative process, so that an image corrected in the above-described manner is again used as an initial image, on which a renewed beam hardening correction is carried out (again) in the manner described. This procedure can be repeated until an adequately low-artefact image is available.

In the exemplary embodiments described herein, bones are cited as the material causing beam hardening. Other materials causing beam hardening are, for example, metals, which may be present as implants or false teeth in a patient.

In a further version of the above-described exemplary embodiment, two threshold values can be used, the relevant pixels then being those pixels which have a pixel value within a range defined by the two threshold values. A procedure of this type is suitable, for example, when the material causing the beam hardening is a contrast agent.

The construction of the image computer 11 in the exemplary embodiments is described in the context of the preprocessing unit 12 and the reconstruction unit 13 being hardware components. Generally, however, the aforementioned components are implemented by software modules which run on a universal computer provided with the requisite interfaces and, differing from FIG. 1, also perform the function of the control unit 18, which is then superfluous.

The CT apparatus in the exemplary embodiments has a detector system 5 having rows each having the same width measured in the z direction (for example, 1 mm). Differing from this, within the context of the invention, a detector system can be provided with rows of respectively different widths. For example, two inner rows each 1 mm wide and, on both sides thereof, a row 2 mm wide can be provided.

In the exemplary embodiments, the relative movement between the measuring unit 1 and the mounting device 9 is produced by the support device 9 being displaced. Within the context of the invention, however, there is also the possibility of leaving the support device 9 in a fixed position and displacing the measuring unit 1 instead. In addition, within the context of the invention, there is the possibility of producing the necessary relative movement by displacing both the measuring unit 1 and the support device 9.

In the exemplary embodiment a CT apparatus of the third generation is described, i.e. the X-ray source and the detector system are displaced together around the system axis during the production of an image. The invention also can be used in connection with CT apparatus of the fourth generation, in which only the X-ray source is displaced around the system axis and interacts with a stationary detector ring, provided the detector system is a two-dimensional array of detector elements.

The invention also can be used with a CT apparatus of the fifth generation, wherein X-rays originate from a number of foci of one or more X-ray sources displaced about the system axis, instead of just from one focus, provided the detector system has a two-dimensional array of detector elements.

The CT apparatus described in the exemplary embodiments has a detector system with detector elements arranged in the manner of an orthogonal matrix. The invention also can be used in connection with a CT apparatus having a detector system with detector elements arranged other than as a two-dimensional array.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for correcting for beam hardening in an initial CT image, composed of pixels arranged in a matrix, comprising the steps of:

obtaining correction data from said initial image by re-projecting the pixels therein at a plurality of projection angles using only pixels from said initial image for each projection angle having a pixel value above a threshold value; and producing a corrected image from said initial image using said correction data.

2. A method as claimed in claim 1 wherein the pixels in said initial image having a pixel value above said threshold value are identified during said re-projection.

3. A method as claimed in claim 1 wherein the pixels in said initial image having a pixel value above said threshold value are determined before re-projecting said pixels, and comprising the steps of storing said pixels from said initial image having a pixel value above said threshold value, as stored pixels, and using said stored pixels for re-projection for each of said projection angles.

4. A method as claimed in claim 3 comprising storing said stored pixels in dataset which, for each of said stored pixels, contains coordinates of a center of each stored pixel and the pixel value of each stored pixel.

5. A method as claimed in claim 3 comprising storing said stored pixels in a data set which, for each of said stored pixels, contains a linear index and a pixel value.

* * * * *